US009593073B2

(12) United States Patent
Proctor

(10) Patent No.: US 9,593,073 B2
(45) Date of Patent: Mar. 14, 2017

(54) METHOD FOR THE PREPARATION OF DIAZOALKANES

(71) Applicant: BAKHU LIMITED, Southport (GB)

(72) Inventor: Lee Proctor, Flintshire (GB)

(73) Assignee: BAKHU LIMITED, Southport (GB)

( * ) Notice: Subject to any disclaimer, the term of this patent is extended or adjusted under 35 U.S.C. 154(b) by 0 days.

(21) Appl. No.: 14/373,828

(22) PCT Filed: Jan. 23, 2013

(86) PCT No.: PCT/GB2013/050141
§ 371 (c)(1),
(2) Date: Jul. 22, 2014

(87) PCT Pub. No.: WO2013/110932
PCT Pub. Date: Aug. 1, 2013

(65) Prior Publication Data

US 2015/0038687 A1 Feb. 5, 2015

(30) Foreign Application Priority Data

Jan. 23, 2012 (GB) .................................. 1201066.6

(51) Int. Cl.
*C07C 245/16* (2006.01)
*C07C 241/00* (2006.01)
*C07C 243/04* (2006.01)

(52) U.S. Cl.
CPC .......... *C07C 241/00* (2013.01); *C07C 243/04* (2013.01); *C07C 245/16* (2013.01); *C07C 2531/02* (2013.01)

(58) Field of Classification Search
CPC .................................................... C07C 245/16
See application file for complete search history.

(56) References Cited

U.S. PATENT DOCUMENTS

| | | | | |
|---|---|---|---|---|
| 3,963,698 | A | 6/1976 | Hecht et al. | |
| 5,817,778 | A | 10/1998 | Archibald et al. | |
| 6,962,983 | B2 * | 11/2005 | Warr et al. | 534/565 |
| 2007/0249817 | A1 | 10/2007 | Haase | |

FOREIGN PATENT DOCUMENTS

WO 0147869 A1 7/2001

OTHER PUBLICATIONS

International Search Report issued in International Patent Application No. PCT/GB2013/050141 mailed on Mar. 22, 2013.
Adamson, et. al., "The preparation of diazomethane and its homologues", Journal of the Chemical Society, Jan. 1, 1935 (p. 286), XP055055758.
Jones, et al., "The catalytic decomposition of nitroso-β-alkylaminoketones. Part I. A new method of preparing diazomethane, and evidence of the occurrence of diazotisation in the aliphatic series", Journal of the Chemical Society, 1933, pp. 363-368.
Adamson et al., "Improved Preparations of Aliphatic Diazo-Compounds,and Certain of Their Properties", Journal of the Chemical Society, pp. 1551-1556, 1937.
Redemann, et al., "Diazomethane", Organic Syntheses, Coll. vol. 3, p. 244 (1955); vol. 25, p. 28 (1945).
Pearce, M., "The Rates of Diazomethane Formation from Methylnitrosoamides. The Stability of Diazomethane Solutions towards Aqueous Alkalis", Helv. Chim. Acta 1980, vol. 63, Issue 4, pp. 887-891.

* cited by examiner

*Primary Examiner* — Robert Havlin
(74) *Attorney, Agent, or Firm* — Brinks Gilson & Lione

(57) ABSTRACT

The present invention relates to a method of forming diazoalkanes. One aspect of the present invention provides a method for the production of a N-alkyl-N-nitroso compound from a starting material, comprising the use of a tribasic acid to acidify an amine. A second aspect of the present invention provides a method for the production of a diazoalkane, comprising reacting a N-alkyl-N-nitroso compound with a base and a phase transfer catalyst, wherein no organic solvent is used.

17 Claims, No Drawings

METHOD FOR THE PREPARATION OF DIAZOALKANES

FIELD OF THE INVENTION

The present invention relates to the production of diazoalkanes. One aspect provides an improved method for producing a diazoalkane from a N-alkyl-N-nitroso compound. An improved method for producing such a N-alkyl-N-nitroso compound is also described. Also provided is a method of forming tert-butyl (S)-4-chloro-3-oxo-1-phenylbutan-2-ylcarbamate (Boc-CK), using diazomethane as produced from the methods of the previous aspects.

BACKGROUND TO THE INVENTION

Diazoalkanes are important compounds in organic synthesis and are commonly used as intermediates or reactants in reactions such as the etherification of NH bonds, OH bonds or acid bonds, or during syntheses of heterocyclic compounds. They are also used in addition and insertion reactions under mild conditions.

Diazomethane is a highly reactive gas with a wide range of uses in chemical syntheses. It is commonly used as a methylating agent for a wide variety of compounds, as well as being used for ring expansion or chain extension of ketones and for the conversion of ketones to epoxides. It is also commonly used in cycloaddition reactions with olefins to produce cyclopropyl or nitrogen-containing heterocyclic rings. Diazomethane also has pharmaceutical implications, for example in the formation of viral protease inhibitors including those to combat HIV, especially where an addition of a carbon atom is required without compromising the chirality of the amino acid or affecting the rest of the molecule.

Diazomethane is a hazardous reagent. It is both a carcinogen and an allergen, as well as being highly poisonous. Further, it is highly explosive, which poses a problem during its synthesis.

The synthesis of diazomethane from N-alkyl-N-nitroso compounds is well-known in the art and often involves the addition of a base. A commonly used N-alkyl-N-nitroso compound is N-nitroso-β-methylaminoisobutyl methyl ketone ("Liquizald"), the preparation of which is also known in the art. Liquizald is usually made from mesityl oxide, which is then reacted with methylamine to create an intermediate amine. This intermediate amine is then treated with acid and a source of nitrite to form Liquizald. Liquizald has various advantages over other commonly used N-alkyl-N-nitroso compounds, such as Diazald, which include stability, cost and availability.

The preparation of Liquizald from mesityl oxide and its use for producing diazomethane was first described by Jones and Kenner (Journal of the Chemical Society, 1933, p 363-368). The method uses monobasic hydrochloric acid to acidify an intermediate amine, although the quantity of acid used is not specified. After acidification, the solution is extracted with diethyl ether to remove residual mesityl oxide and the Liquizald product is distilled. This distillation is potentially hazardous as the product is reported to be unstable when heated.

Diazomethane was generated from the purified Liquizald by reacting a solution of Liquizald in diethyl ether with various sodium alkoxides generated from ethanol, isopropanol, n-propanol, sec-butyl alcohol, methylpropylcarbinol and tertiary butyl alcohol and heating the solution to recover an ethereal solution of diazomethane. Yields ranged from 0% (using the sodium salt of tert-butanol) to 83.5% (using the sodium salt of isopropanol).

In a subsequent publication, Adamson and Kenner (Journal of the Chemical Society, 1937, p1551-1556) describe an improved method for generating Liquizald in which monobasic acetic acid is used. This method formed the basis of an Organic Synthesis publication (Organic Synthesis, Coll Vol. 3 p. 244 (1955); Vol. 25, p. 28 (1945)). The method generated Liquizald with a yield of 70-80% based on mesityl oxide but required back extraction using diethyl ether to achieve this yield.

The generation of diazomethane was described using sodium isopropoxide in isopropanol/ether at 70-75° C., giving a diazomethane yield of 45-60%. A second method is described using sodium cyclohexoxide in cyclohexanol/ether at 50-55° C., which gave a diazomethane yield of 77-84%. A method for generating gaseous diazomethane is also described, by reacting an anisole solution of Liquizald with sodium cyclohexoxide to give a diazomethane yield of 65%.

U.S. Pat. No. 5,817,778 describes the use of phase transfer catalysis for generating diazomethane from a N-alkyl-N-nitroso compound in an organic solvent. The phase transfer catalyst enhances the rate of reaction between a reactant in the aqueous phase and one in the organic phase. The solvent is used to prevent the detonation of the diazomethane and is co-distilled with the diazomethane so that the amount of diazomethane within the vapour produced is maintained within safe limits. However, the N-alkyl-N-nitroso compound defined in U.S. Pat. No. 5,817,778 does not include Liquizald.

WO00147869 discloses a continuous method for generating diazomethane from a N-alkyl-N-nitroso compound, with Liquizald as an exemplary N-alkyl-N-nitroso compound, in a solvent such as DMSO.

US2007/0249817 refers to the WO patent above but describes a method for removing the produced diazomethane as a gas, using reduced pressure.

U.S. Pat. No. 3,963,698 discloses the use of N-methyl-N-nitrosourea in a 1,2-dimethoxyethane and water solution, in the presence of a base, to produce diazomethane. In this reaction, 1,2-dimethoxyethane is used as a solvent and is present at a ratio to water of 5:1, thereby creating a single phase homogeneous solution.

The decomposition of Liquizald to form diazomethane is also disclosed in Helv Chim Acta (Vol 63(4), 1980, p887-891), where the use of potassium hydroxide at low temperatures in the presence of toluene is disclosed.

The importance of diazomethane as a reactant and an intermediate in many chemical reactions, as well as its toxicity and explosiveness, means that there is a need for methods that create diazomethane at high yields but also maintain the required safety standards. Safety could be increased by eliminating the need for a distillation step. Further, the use of certain organic solvents can pose environmental and waste disposal problems, so eliminating the need for such solvents would also be beneficial.

While the invention will be described in connection with certain preferred embodiments, it is not intended to limit the invention to the particular embodiments. On the contrary, it is intended to cover all alternatives, modifications and equivalent methods as may be included within the scope of the invention as defined by the appended claims.

SUMMARY OF THE INVENTION

One aspect of the present invention provides a method for the production of a diazoalkane, comprising reacting a N-alkyl-N-nitroso compound with a base and a phase transfer catalyst, wherein no organic solvent is used.

A phase transfer catalyst is defined as a catalyst that facilitates the migration of a reactant from one phase into another phase, where reaction occurs. Phase transfer catalysis is a special form of heterogeneous catalysis.

In one embodiment, the phase transfer catalyst is tetrabutyl ammonium bromide (TBAB). In further embodiments, the TBAB is used at a loading of more than 0.1 mol %, preferably between 0.1 mol % and 2 mol %, more preferably between 0.1 mol % and 1 mol % and most preferably 1 mol %.

In other embodiments, the reaction occurs at a temperature of between 0° C. and 40° C., preferably between 0° C. and 20° C. and most preferably between 0° C. and 10° C. In a further embodiment, the reaction occurs at a temperature of 10° C. The lower temperatures in these ranges are safer and limit the quantity of water vapour in the diazomethane/nitrogen gas stream.

In one embodiment, the base is present at a concentration of between 10% and 50% w/w. The base is preferably present at a concentration of 50% w/w. The use of such a concentration acts to stabilise the resulting diazoalkane, with the half-life of the diazoalkane increasing with increasing concentration. For example, diazomethane has a half life of around 35 seconds in water, while the half life in 50% NaOH is 28880 seconds (8 hours).

In other embodiments, the reaction occurs in the presence of water.

The yield of the diazoalkane with the method of the present invention is high. In some embodiments, the yield of the diazoalkane is above 75%. Preferably, the yield of the diazoalkane is approximately 90%.

In one embodiment, the diazoalkane is diazomethane. In other embodiments, the N-alkyl-N-nitroso compound is a N-methyl-N-nitroso compound. In other embodiments, the N-alkyl-N-nitroso compound has the general formula:

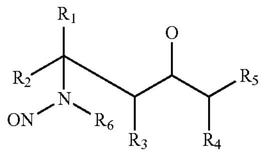

wherein $R^1$, $R^2$, $R^3$ and $R^4$ are hydrogen, alkyl, alkenyl, alkoxy, alkoxylate, alkyloxy, alkenyloxy or alkoxyalkyl groups, $R^6$ is an alkyl group and $R^5$ is $OR^7$, $NR^7$ or $R^7$, wherein $R^7$ is hydrogen or an alkyl group.

In some embodiments of the present invention, when $R^5$ is $R^7$, an organic by-product is formed in the production of the diazoalkane, which separates from the reaction mixture as a discrete phase. Preferably, the organic by-product does not require purification after it has been recovered from the reaction mixture. In other embodiments, this by-product can then be used to produce a further N-alkyl-N-nitroso compound.

In other embodiments, the organic by-product has the general formula:

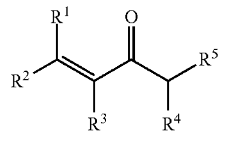

wherein $R^1$, $R^2$, $R^3$ and $R^4$ are hydrogen, alkyl, alkenyl, alkoxy, alkoxylate, alkyloxy, alkenyloxy or alkoxyalkyl groups and $R^5$ is $OR^7$, $NR^7$ or $R^7$, wherein $R^7$ is hydrogen or an alkyl group. In further embodiments, the N-alkyl-N-nitroso compound is N-nitroso-β-methylaminoisobutyl methyl ketone (Liquizald), the organic by-product is mesityl oxide and/or the diazoalkane is diazomethane.

Another aspect of the present invention relates to a method for the production of a N-alkyl-N-nitroso compound from a starting material, comprising the use of a tribasic acid to acidify an amine. The use of a tribasic acid reduces, and preferably eliminates, the acid contamination in the resulting product.

In other embodiments, the tribasic acid is phosphoric acid. In further embodiments, the phosphoric acid is at a concentration of between 60% and 80% in an aqueous solution. Preferably, the phosphoric acid is at a concentration of 75% in an aqueous solution.

The yield of the N-alkyl-N-nitroso compound using the method of the present invention is high. Preferably, the yield of the N-alkyl-N-nitroso compound is approximately 80%.

In further embodiments, the reaction is such that the sodium phosphate salts produced as a by-product are close to saturation in the aqueous phase. Preferably, the reaction occurs at a temperature of between 15° C. and 25° C. during the stir out and separation stages. In still further embodiments of the present invention, the N-alkyl-N-nitroso compound separates from the reaction mixture as a discrete phase.

In other embodiments, the N-alkyl-N-nitroso compound can be easily separated from the reaction mixture, without the use of an organic solvent. In other embodiments, there is no need for purification of the N-alkyl-N-nitroso compound after it has been recovered.

In other embodiments, the starting material has the general formula:

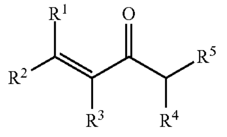

wherein $R^1$, $R^2$, $R^3$ and $R^4$ are hydrogen, alkyl, alkenyl, alkoxy, alkoxylate, alkyloxy, alkenyloxy or alkoxyalkyl groups and $R^5$ is $OR^7$, $NR^7$ or $R^7$, wherein $R^7$ is hydrogen or an alkyl group.

In one embodiment, the N-alkyl-N-nitroso compound is a N-methyl-N-nitroso compound. In other embodiments, the N-alkyl-N-nitroso compound has the general formula:

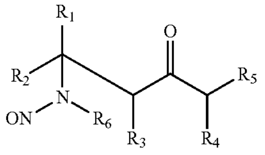

wherein $R^1$, $R^2$, $R^3$ and $R^4$ are hydrogen, alkyl, alkenyl, alkoxy, alkoxylate, alkyloxy, alkenyloxy or alkoxyalkyl groups, $R^6$ is an alkyl group and $R^5$ is $OR^7$, $NR^7$ or $R^7$, wherein $R^7$ is hydrogen or an alkyl group. In still further embodiments, the N-alkyl-N-nitroso compound is Liquizald and/or the starting material is mesityl oxide.

Another aspect of the present invention relates to a method of forming a diazoalkane from a starting material, comprising the methods of the two previous aspects. In one embodiment, the product of the first aspect does not need to be purified before use in the method of the second aspect.

In some embodiments, when $R^5$ is $R^7$, the starting material is formed in the production of the diazoalkane and separates from the reaction mixture as a discrete phase. Preferably, the starting material does not require purification after it has been recovered from the reaction mixture. In further embodiments, the starting material is mesityl oxide, an intermediate is Liquizald and/or the diazoalkane is diazomethane.

A final aspect of the present invention provides a method of forming tert-butyl (S)-4-chloro-3-oxo-1-phenylbutan-2-ylcarbamate (Boc-CK), using diazomethane as produced from the methods of the previous aspects.

DETAILED DESCRIPTION OF THE PREFERRED EMBODIMENTS

Preparation of a Diazoalkane from a N-alkyl-N-nitroso Compound

Scheme 1

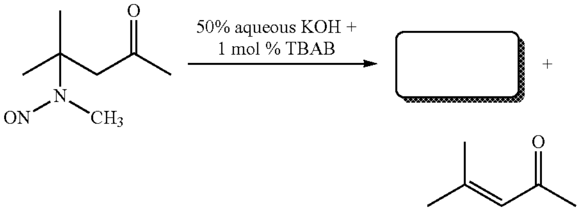

mesityl oxide

The preparation of a diazoalkane from a N-alkyl-N-nitroso compound using a base is well known in the prior art. An exemplary method for the preparation of a diazoalkane according to the present invention is outlined in Scheme 1 above. In the above embodiment, the diazoalkane is diazomethane, the N-alkyl-N-nitroso compound is Liquizald and the organic by-product of the reaction is mesityl oxide. The above method can be done continuously or in batches.

The present invention includes the use of a phase transfer catalyst. The phase transfer catalyst is preferably present at a catalytic amount. Any known phase transfer catalyst can be used, such as quaternary ammonium, phosphonium salts, crown ethers and glycol ethers. Preferably, this phase transfer catalyst is TBAB. In one embodiment, TBAB is present at a loading of 1 mol %, though any loading of more than 0.1 mol %, preferably between 0.1 mol % and 2 mol % and even more preferably between 0.1 mol % and 1 mol % may be used. The phase transfer catalyst has been shown to advantageously affect the yield, significantly increasing the yield when compared to the yield of reactions without the catalyst.

The above reaction occurs without the presence of organic solvents, which were previously thought to be necessary. Further, there is no need for the use of organic solvents to separate the reaction products after the reaction and no purification steps are necessary. The elimination of the need for organic solvents not only reduces the cost of the method of the present invention compared to those of the prior art, but also has advantageous environmental and waste disposal implications.

In other embodiments, when $R^5$ is $R^7$, the organic by-product of the diazoalkane formation separates from the reaction mixture as a less dense upper phase, after the production of the diazoalkane. In a further preferred embodiment, the organic by-product can be easily removed from the reaction mixture by simple liquid-liquid separation. This is possible as there are no other organic compounds within the reaction mixture. In a further preferred embodiment, the organic by-product recovered in this manner is identical to the fresh material, as analysed by $^1H$ NMR, and so can be recycled.

The base used in the above reaction can be any inorganic alkali metal base. Preferably, the base is sodium or potassium hydroxide. The base can be present at a concentration of between 10% and 50% w/w, preferably 50% w/w. Most preferably, the base is 50% aqueous potassium hydroxide.

In one embodiment, the reaction occurs at a temperature of between 0° C. and 40° C., preferably between 0° C. and 20° C. and most preferably between 0° C. and 10° C. In a further embodiment, the reaction occurs at a temperature of 10° C.

The yield of the diazoalkane from the above method is high. Preferably, the yield is above 75%. More preferably, the yield is around 90%.

The diazoalkane product is preferably produced as a gas, so as to allow for convenient separation of the diazoalkane product and the reaction mixture. In a further embodiment, the diazoalkane may be collected in combination with nitrogen, due to nitrogen sparging.

In one embodiment of the present invention, the above reaction is carried out with continual sparging with nitrogen gas sub-surface. Such sparging aids the mixing of the reaction mixture and helps displace the diazoalkane gas from the reaction mixture. Preferably, the flow rates of the sparge diluent gas are such that the concentration of the diazoalkane gas is maintained below an explosive level, especially when the diazoalkane is diazomethane. When the sparge diluent gas is nitrogen, the concentration of diazomethane in nitrogen is preferably below the explosive limit of 14.7%.

In further embodiments, the above method is carried out at atmospheric pressure. In still further embodiments, the above method is carried out at a sub-atmospheric pressure.

In one embodiment of the present invention, as shown in Scheme 1, Liquizald is treated with 50% aqueous potassium hydroxide and 1 mol % TBAB at a temperature of less than 10° C., to form diazomethane and mesityl oxide. Gas sparging with nitrogen gas sub-surface occurs continuously throughout the method.

Preparation of a N-alkyl-N-nitroso Compound

Scheme 2

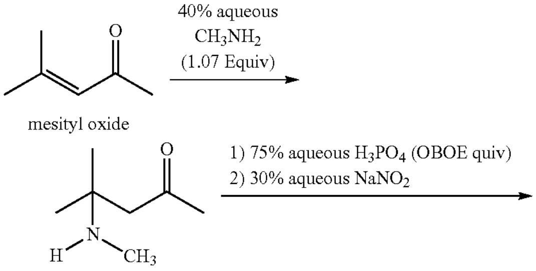

-continued

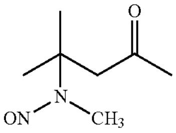

N-nitroso-β-methylaminoisobutyl methyl ketone (Liquizaid)

The general method of adding an aliphatic amine to a starting material to form an intermediate amine, followed by the addition of an acid and an alkali metal nitrite to prepare a N-alkyl-N-nitroso compound is well known in the art. An exemplary method for the preparation of a N-alkyl-N-nitroso compound according to the present invention is outlined in Scheme 2 above. In the above embodiment, the N-alkyl-N-nitroso compound is Liquizald and the starting material is mesityl oxide. The above method can be done continuously or in batches.

One aspect of the present invention involves the use of a tribasic acid to acidify an amine. Any tribasic acid may be used, such as phosphoric acid or citric acid. In a further embodiment, the tribasic acid is phosphoric acid. Preferably, the phosphoric acid is between 60% and 80% aqueous phosphoric acid, most preferably 75% aqueous phosphoric acid. It has been found that the use of a tribasic acid surprisingly reduces the acid contamination of the N-alkyl-N-nitroso product, as sub-stoichiometric quantities of acid can be used. Preferably, the acid contamination of the product is eliminated.

Further, the yield of the above method has been shown to be high compared to the methods of the prior art. Preferably, the yield of the N-alkyl-N-nitroso compound is around 80%, without the need for an extraction step.

Another aspect of the invention relates to the above method that does not include a purification step or an extraction step in order to obtain the end product. Instead, the N-alkyl-N-nitroso compound separates out from the reaction mixture after ageing as an upper organic phase. This is optimised by the fact that the sodium phosphate salts produced as a by-product of the reaction are close to saturation in the aqueous phase. The high level of salt saturation reduces the solubility of the N-alkyl-N-nitroso compound in the aqueous phase, ensuring high yields and clean separation of the product. The product can then be easily removed from the reaction mixture, without the use of further methods that may involve an additional organic solvent or a distillation reaction. Preferably, the reaction occurs at a temperature of between 15° C. and 25° C. during the stir out and separation stages.

In one embodiment of the present invention, as shown in Scheme 2, mesityl oxide is reacted with 40% aqueous methylamine to form an intermediate amine. The intermediate amine is acidified with 75% aqueous phosphoric acid and then reacted with 30% aqueous sodium nitrite. Liquizald separates out from the reaction mixture after aging as an upper organic phase.

Reagents suitable for use in the above method, such as alternative aliphatic amines, are well-known in the art. The preferred reagents for use in the above reaction are outlined in Table 1.

TABLE 1

| Chemical | MW | Source/Lot number | Wt (g) | Strength (%) | Moles | Equiv |
|---|---|---|---|---|---|---|
| Mesityl oxide | 98.14 | Acros 271933 | 300 g | 89.9%* | 2.75 | 1.00 |
| Methylamine (39.7%) | 31.06 | Sigma S57254-448 | 230 g | 39.7% aq solution | 2.94 | 1.07 |
| Phosphoric acid (75%) | 98.00 | Aldrich S67971-039 | 310.2 g | 75% | 2.37 | 0.86 |
| Sodium nitrite (30%) | 69.00 | Sigma 26430JB | 771.3 g | 30% | 3.35 | 1.22 |

*Ratio of β/α isomers by $^1H$ NMR

Preparation of a Diazoalkane from a Starting Material with a N-Alkyl-N-Nitroso Compound Intermediate In a further aspect of the present invention, there is provided a method for the preparation of a diazoalkane from a starting material, with a N-alkyl-N-nitroso compound as an intermediate, comprising the reactions of the previous two aspects. In one embodiment, the starting material is mesityl oxide, an intermediate is Liquizald and the diazoalkane is diazomethane, as shown in Schemes 1 and 2.

One embodiment of the present invention provides that, when $R^5$ is $R^7$, the starting material separates from the reaction mixture as a less dense upper phase, after the production of the diazoalkane. In a further preferred embodiment, the starting material can be easily removed from the reaction mixture by simple liquid-liquid separation. In a further preferred embodiment, the starting material recovered in this manner is identical to fresh material, as analysed by $^1H$ NMR. This starting material can then be used in subsequent reactions, without the need for purification.

In further embodiments, the above method is carried out at atmospheric pressure. In still further embodiments, the above method is carried out at a sub-atmospheric pressure.

The method of the present invention is cheaper than those disclosed in the prior art. For example, the method disclosed in WO01/47869 produces diazomethane at a cost of around £4.15 per mol. In contrast, the present invention produces diazomethane at a cost of around £0.62 per mol without mesityl oxide recycling and £0.28 per mol with mesityl oxide recycling.

Method for producing tert-butyl (S)-4-chloro-3-oxo-1-phenylbutan-2-ylcarbamate (Boc-CK) using diazomethane Scheme 3

Stage 1 mixed anhydride

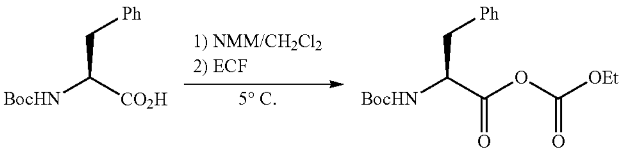

Boc-MA

-continued

Stage 2b diazoketone

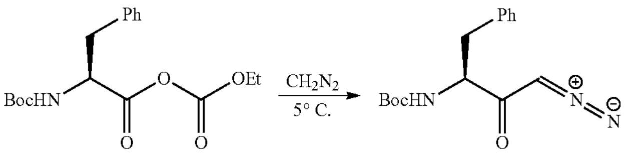

Boc-DAK

Stage 3 chloroketone

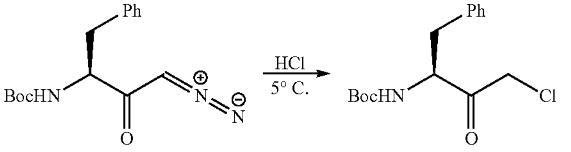

Boc-CK

Stage 2a diazomethane

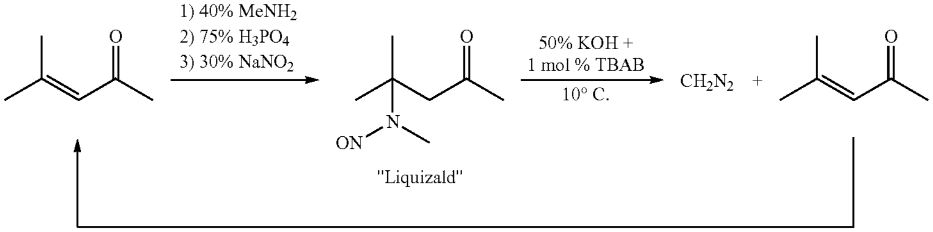

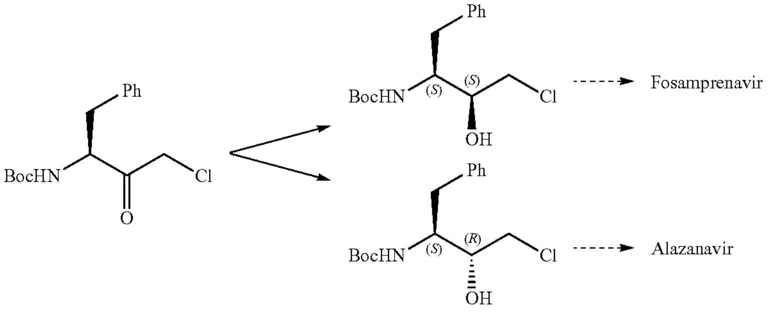

In a final aspect of the present invention, there is provided a method of producing tert-butyl (S)-4-chloro-3-oxo-1-phenylbutan-2-ylcarbamate (Boc-CK), using diazomethane produced from the methods of the previous examples. Boc-CK is an intermediate used for the production of HIV protease inhibitors, such as Atazanavir and Fosamprenavir.

In one embodiment, the diazomethane is produced from Liquizald, as shown in Scheme 3 above. The diazomethane produced from the reactions of the present invention is in the gas phase and so the above reactions can occur with substrates in different solvents if desired. This further demonstrates the versatility and the utility of the reaction of the present invention.

Examples

Preparation of Liquizald

A 2 L glass reactor was equipped with a 500 mL addition funnel, agitator, thermometer and cooling bath.

1. The reactor was charged with 39.7% aqueous methylamine solution (230 g) and cooled to 10° C.
2. When the temperature reached 7° C., addition of mesityl oxide (300 g) was started. The temperature was controlled at between 10° C. and 15° C. Total addition time was 57 minutes.
3. The clear pale orange solution was warmed to 22° C. over 5 minutes and then stirred at this temperature for 60 minutes.
4. The solution was cooled to 10° C. over 5 minutes. 75% Phosphoric acid (310.2 g) was added over 60 minutes. The temperature was maintained between 15° C. and 20° C. During the addition the mixture became more viscous. The pH at the end of the addition was 6.65.
5. 30% aqueous sodium nitrite (771.3 g) was added over 8 minutes at between 10° C. and 15° C.
6. The mixture was stirred at between 20° C. and 25° C. for 18.3 hours and then settled for 1 hour.
7. The lower aqueous phase (1122 g, pH=5.76) was separated from the upper product Liquizald phase (466.6 g, 73.4% active, 79% yield from mesityl oxide). The Liquizald phase was analysed by $^1H$ NMR in d6-DMSO, the results of which are shown in Table 2.

TABLE 2

| Compound | % w/w by NMR |
|---|---|
| Mesityl oxide | 8.6% |
| Liquizald | 73.4% |
| Water | 18.3% |

This process is both robust and reproducible, as demonstrated in Table 3 below. This table shows the results of four additional repeats of the above method.

TABLE 3

| | Crude | Active Molar | Assay (% w/w NMR) | | |
|---|---|---|---|---|---|
| Experiment | Yield (g) | Yield (%) | Liquizald (%) | Mesityl Oxide (%) | Water (%) |
| 1 | 483.5 g | 86.7% | 78.1% | 9.3% | 12.6% |
| 2 | 480.0 g | 89.7% | 81.3% | 11.8% | 6.9% |
| 3 | 469.8 g | 80.3% | 74.3% | 11.9% | 13.7% |
| 4 | 466.6 g | 79.0% | 73.4% | 8.6% | 18.0% |

This is in contrast to when a mono- or a di-basic acid is used. For example, when the above method was carried out with acetic acid instead of phosphoric acid, the Liquizald produced had the composition by $^{1}H$ NMR as shown in Table 4 below. The use of the Liquizald phase of Table 2 resulted in a 39% higher yield of diazomethane than when using the phase as outlined in Table 4.

TABLE 4

| Component | Assay (% w/w by NMR) |
|---|---|
| Mesityl oxide | 13.1% |
| Liquizald | 79.5% |
| Water | 1.0% |
| Acetic acid | 6.4% |

The Liquizald phase produced by the above method can be used in the preparation of diazomethane from Liquizald, as discussed below, without any further purification steps.

Preparation of Diazomethane from Liquizald

A 100 mL reaction vessel was charged with 50% aqueous potassium hydroxide solution (10.0 g) and tetrabutyl ammonium bromide (TBAB) phase transfer catalyst. The solution was cooled to 10° C. whilst stirring. Liquizald (10.0 g) was added to the solution over 60 minutes and the reaction temperature was maintained at 10° C. whilst continually sparging with nitrogen gas sub-surface. The vent gases were sparged into 100 mL of 1 M benzoic acid in dimethoxyethane (DME). Once addition of Liquizald was complete, nitrogen sparging was continued for an additional 30 minutes. The concentration of residual benzoic acid was determined by titrating the DME solution with 0.5 M sodium hydroxide using phenolphthalein indicator. The yield of diazomethane was determined from the consumption of benzoic acid.

Runs 1 to 4, as shown below in Table 5, used 1.0, 0.5, 0.1 and 0.0 mol % TBAB respectively. Run 5 used 1.0 mol % TBAB but achieved mass transfer of diazomethane by application of a vacuum (200 mbar) and a reduced nitrogen flow rate of 0.05 L/min. The resulting yields are shown in Table 5.

TABLE 5

| Run | TBAB Loading (mol %) | Temperature (° C.) | Nitrogen Flow (L/min) | Diazomethane Yield (%) |
|---|---|---|---|---|
| 1 | 1.0 mol % | 10° C. | 0.5 L/min | 90.6% |
| 2 | 0.5 mol % | 10° C. | 0.5 L/min | 86.8% |
| 3 | 0.1 mol % | 10° C. | 0.5 L/min | 79.8% |
| 4 | 0.0 mol % | 10° C. | 0.5 L/min | 2.2% |
| 5 | 1.0 mol % | 10° C. | 0.05 L/min and 200 mbar vacuum | 92.7% |

As shown in Table 5, the concentration of TBAB has a significant effect on the diazomethane yield, with the maximum yield being obtained at a TBAB loading of 1.0 mol %.

Preparation of Diazomethane from Liquizald at Different Reaction Temperatures—Kinetic Analysis All kinetic experiments were conducted using a 50 mL 3-neck round vessel equipped with a 15 mm×10 mm magnetic stirrer bar. The vessel was charged with 50% KOH (20 g) and TBAB (0.3 g). The mixture was equilibrated to the desired reaction temperature over 10 to 15 minutes whilst being agitated at around 1000 rpm and sparged sub-surface with nitrogen at a rate of 0.55 L/min. The nitrogen residence time in the headspace was calculated to be 2.9 seconds.

Liquizald (10 g crude, 7.34 g active) was added in one portion. The exiting diazomethane/nitrogen gas stream was bubbled into a solution of benzoic acid (6.0 g) in dichloromethane (150 mL) cooled to around 5° C. in a 500 mL vessel. The conversion of benzoic acid to methyl benzoate was continually monitored using a Mettler Toledo SiComp attenuated total reflectance ReactIR probe with a sampling interval of 60 seconds.

Each reaction showed an induction period of between 1 and 6 minutes, which were entirely consistent with other hydroxide ion initiated reactions under phase transfer catalysed conditions (for example Org. Chem. 1983, 48, 1022-1025). The induction arises from the need for the $[Q^{+}OH^{-}]$ ion pair to reach an equilibrium concentration in the organic phase. The reactions followed pseudo first order kinetics after the initial induction period, with an activation energy (Ea) of 69.5 kJ $mol^{31\ 1}$ (16.6 kcal $mol^{-1}$) and the pre-exponential factor (A) of $9.18\times10^{9}$ $mol^{-1}s^{-1}$. The half-lives across the temperature range investigated are shown in Table 6 below, along with the induction periods:

TABLE 6

| Temperature ° C. | Half-life (mins) | Induction Period (mins) |
|---|---|---|
| 0 | 30.8 | ~5.5 |
| 10 | 8.0 | ~3.5 |
| 20 | 2.1 | ~2.5 |
| 30 | 1.2 | ~1.5 |
| 40 | 0.6 | ~1.5 |

Preparation of Diazomethane from Liquizald at Scale

An appropriate glass-lined reaction vessel was charged with 50% KOH solution (1296 kg). TBAB catalyst (26.4 kg, 2 mol %) was then charged. The vessel contents were cooled to 10° C. and well agitated. Nitrogen gas was added sub-surface at a rate of 8 kg/hr and into the headspace of the vessel at a rate of 34 kg/hr. Liquizald (as 100% active) was added at a rate of 27 kg/hr. The exiting diazomethane/nitrogen gas stream was at a concentration of 10% v/v. The gas stream was passed through a gas-liquid separator and a packed scrubber tower attached to the vessel. A solution of substrate (for example Boc-mixed anhydride) flowed on a continuous recycle loop through the scrubber tower from a second vessel. At 10° C., the half-life of Liquizald is 8 minutes and with a Liquizald feed rate of 27 kg/hr there was no accumulation of Liquizald in the vessel.

Diazomethane generated by this process is capable of converting 542 kg of Boc-mixed anhydride (as 100% active) in a 24 hour period.

Production of tert-butyl (S)-4-chloro-3-oxo-1-phenylbutan-2-ylcarbamate (Boc-CK), an Intermediate Used for the Production of HIV Protease Inhibitors Such as Atazanavir and Fosamprenavir, Using Diazomethane Generated from Liquizald

Preparation of Boc-Mixed Anhydride

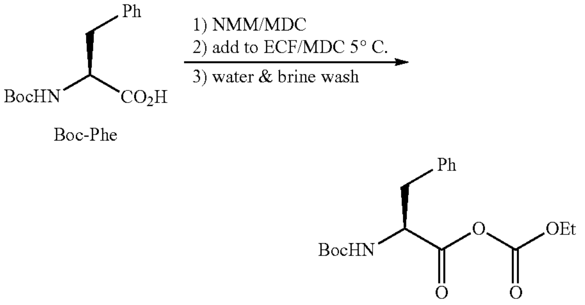

Boc-Phe

Boc-MA

A 250 mL glass reactor was equipped with a 250 mL addition funnel, agitator, thermometer and cooling bath.

1. Boc-Phe (20.93 g) was dissolved in dichloromethane (100 mL) in a conical flask. N-methylmorpholine (8.78 g) was added in one portion with stirring. The clear colourless solution was transferred to the addition funnel.
2. The reactor was charged with a solution of ethyl chloroformate (10.27 g) in dichloromethane (42 mL) and cooled to between 5° C. and 10° C.
3. Boc-Phe/NMM/dichloromethane was added over 2 minutes at 5° C. to 10° C. Once addition was complete the mixture was stirred for 5 minutes.
4. The reaction mixture which contained white solids of precipitated N-methylmorpholine hydrochloride was transferred into a 500 mL separating funnel. The mixture was washed with water (50 g) and then brine (50 g). The lower clear colourless mixed anhydride solution was transferred into a 500 mL reaction vessel and used as described below.
5. A sample was analysed by HPLC which indicated an area % response of 98.3% for Boc-MA.

Preparation of Diazomethane and Boc-Diazoketone

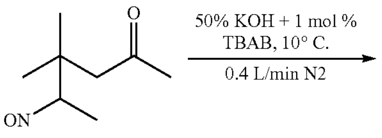

Liquizald

-continued

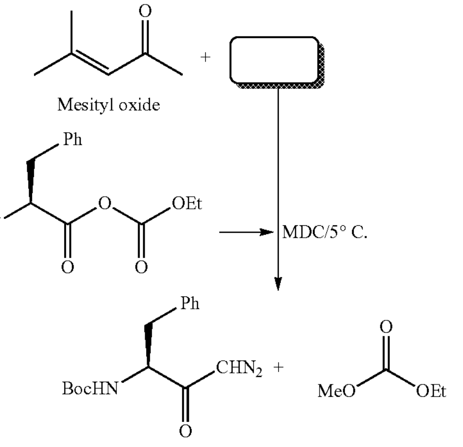

Mesityl oxide

N Boc-DAK methylethylcarbonate

1. A 250 mL 3-neck vessel was equipped with a magnetic stirrer, nitrogen sparge tube, Liquizald addition syringe pump and diazomethane vent sparge pipe. The vessel was charged with 50% KOH solution (50 g) and TBAB (0.75 g) and the mixture cooled to 10° C.
2. Nitrogen gas was sparged into the solution using a porosity 2 sinter at a flow rate of 0.4 L/min (controlled by a VA meter).
3. Liquizald (50 g) was added using a syringe pump over 120 minutes (flow rate=0.42 g/min).
4. The diazomethane/nitrogen gas produced in the reactor was vented via a porosity 2 sinter into a 500 mL 3-neck vessel charged with the mixed anhydride solution prepared above. The reaction temperature was maintained at 5° C. The vessel was equipped with a magnetic stirrer and dry-ice condenser. Note: the condenser vent gases were analysed using a type 1301 photoacoustic FT-IR gas analyser for residual diazomethane.

Once addition of Liquizald was complete the sparging of nitrogen was continued for 25 minutes. The clear pale yellow diazoketone solution was stirred at 5° C. for a further 2 hours. HPLC analysis indicated an area % response of 96.9% for Boc-DAK. The DAK was used directly in the next stage.

Preparation of Boc-Chloroketone from Boc-Diazoketone

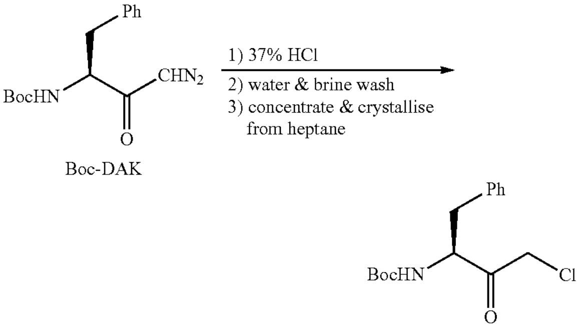

Boc-DAK

Boc-CK

1. The Boc-DAK solution from the previous method was cooled to 5° C. Concentrated (37%) hydrochloric acid was added in small aliquots. After 14.0 g of acid had been added, all the Boc-DAK had been consumed. Note nitrogen gas was evolved during HCl addition.

2. The clear pale yellow solution was transferred into a 500 mL separating flask. The lower product solution was separated from the upper orange aqueous phase (8.3 g, pH<1).
3. The product phase was washed with water (50 mL). The aqueous wash had a pH of around 7.
4. The product solution was washed with brine (50 mL).
5. The clear pale yellow Boc-CK solution (237.7 g) was concentrated to afford a thick yellow slurry (61.7 g).
6. The slurry was mixed with heptanes (158 g) and warmed to 65° C. to dissolve all solids. The clear pale yellow solution was cooled initially to ambient temperature and then further cooled for one hour at 0° C. to 5° C.
7. A very thick white crystalline mass had formed which was filtered through a 54 micron paper using a Buchner filter. The cake was washed with pre-chilled heptanes (2×25 g) and then sucked dry on the filter for 21 hours.
8. Boc-CK (19.6 g) was obtained as a white solid with an area % response by HPLC of 97.2%. Molar yield from Boc-Phe=81.1% (based on the area % assay).

Preparation of Boc-Mixed Anhydride in Toluene

A 1500 mL glass reactor was equipped with a 500 mL addition funnel, agitator, thermometer and cooling bath.

1. Boc-Phe (63 g) was dissolved/suspended in toluene (354 mL) in a conical flask. N-methylmorpholine (26.4 g) was added in one portion with stirring. The clear colourless solution was transferred to the addition funnel.
2. The reactor was charged with a solution of ethyl chloroformate (30.9 g) in toluene (300 mL) and cooled to between 5° and 10° C.
3. The Boc-Phe/NMM/toluene solution was then added over 2 minutes at 50 to 10° C. Once addition was complete, the mixture was stirred for 5 minutes.
4. The reaction mixture which contained white solids of precipitated N-methylmorpholine hydrochloride was transferred into a 2000 mL separating funnel. The mixture was washed with water (250 mL) and then brine (250 mL). The upper slightly cloudy colourless mixed anhydride phase was dried using around 3 g of anhydrous magnesium sulphate to give a clear colourless solution of Boc-mixed anhydride, which was transferred to a 1000 mL reaction vessel and used as described below.

Preparation of Diazomethane and Boc-Diazoketone in Toluene

1. A 500 mL 3-neck vessel was equipped with a magnetic stirrer, nitrogen sparge tube, Liquizald addition syringe pump and diazomethane vent sparge pipe. The vessel was charged with 50% KOH solution (216 g) and TBAB (4.4 g). The TBAB did not dissolve. The mixture was cooled using an ice/water bath to 10° C.
2. Nitrogen gas was sparged into the solution sub-surface using a porosity 2 sinter at a flow rate of 600 mL/min (controlled by a VA meter).
3. Liquizald (146.6 g) was added using a syringe pump over 4 hours (with a flow rate of 36.3 g/hr).
4. The diazomethane/nitrogen gas produced in the reactor was vented via a 3 mm id glass pipe into a 1000 mL 3-neck vessel charged with the Boc-mixed anhydride solution prepared above. The reaction temperature was maintained at 5° C. The vessel was equipped with a magnetic stirrer, dry-ice condenser and SiComp ReactIR probe. On-line FTIR spectra were collected at 1 minute intervals. The condenser vent gases were analysed using a type 1301 photoacoustic FT-IR gas analyser for residual diazomethane.
5. Samples of the MA/DAK reaction solution were taken for HPLC analysis at regular intervals throughout the four hour Liquizald addition.
6. Once Liquizald addition was complete, sparging of nitrogen was continued until the ReactIR profile remained level. Both on-line ReactIR data and off-line HPLC data indicated smooth conversion. The ReactIR profiles flattened approximately 3 hours after the Liquizald feed had stopped. No diazomethane was observed in solution by ReactIR. The vent gases were analysed using a 1301 photoacoustic gas analyser. This indicated a low parts per million concentration of diazomethane in the vent to scrubber.

Preparation of Diazomethane and Boc-Chloroketone from Boc-Diazoketone in Toluene 1. The Boc-DAK solution prepared above was cooled to 5° C. Concentrated (37%) hydrochloric acid was added in 4.68 g aliquots and after each addition the reaction mixture was sampled for HPLC analysis. After 24.4 g of acid had been added, all of the Boc-DAK had been consumed. Nitrogen gas was evolved after each aliquot of HCl was added.
2. The clear pale yellow solution was transferred into a 2000 mL separating flask. The lower aqueous phase was separated (17 g, pH<1).
3. The product phase was washed sequentially with water (100 mL):

| Wash | Volume (mL) | pH |
|---|---|---|
| 1 | 100 mL | 1.5 |
| 2 | 100 mL | 2.7 |
| 3 | 100 mL | 5.3 |
| 4 | 100 mL | 6.4 |

4. The clear pale yellow Boc-CK toluene solution (620.8 g) was concentrated to 200 g using a RFE at a bath temperature of 43° C. under vacuum. The straw yellow solution was initially cooled to 20° C. and held for three hours after which time a solid crystalline mass had formed. The mixture was cooled to −10° C. for two hours and then filtered and the cake sucked dry overnight. Boc-CK (61 g) was obtained as a white solid with an area % response by HPLC of 89%. The molar yield from Boc-Phe was 76% (based on the area % assay).

The invention claimed is:

1. A method for the production of a diazoalkane, comprising reacting an N-alkyl-N-nitroso compound with a base and a phase transfer catalyst in a reaction mixture, wherein no organic solvent is used;

the phase transfer catalyst is selected from the group consisting of quaternary ammonium salts and phosphonium salts;

the N-alkyl-N- nitroso compound has the general formula:

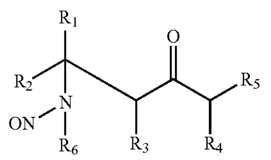

wherein RI, R2, R3 and R4 are hydrogen, alkyl, alkenyl, alkoxy, alkoxylate, alkyloxy, alkenyloxy or alkoxyalkyl groups, R6 is an alkyl group and $R^5$ is hydrogen or an alkyl group; and an organic by-product which is formed during diazoalkane production separates from the reaction mixture as a discrete phase, and wherein said base is present in aqueous solution at a concentration of between 10% and 50%.

2. The method according to claim 1, wherein the phase transfer catalyst is tetrabutyl ammonium bromide (TBAB).

3. The method according to claim 2, wherein the TBAB is used at a loading of between 0.1 mol % and 2 mol %.

4. The method according to claim 3, wherein the TBAB is used at a loading of 1 mol %.

5. The method according to claim 1, wherein the reaction occurs at a temperature of between 0 and 20 C.

6. The method according to claim 1, wherein the reaction occurs at a temperature of less than 10° C.

7. The method according to claim 5, wherein the reaction occurs at a temperature of 10° C.

8. The method according to claim 1, wherein the base is present at a concentration of 50% w/w.

9. The method according to claim 1, wherein the yield of the diazoalkane is above 75%.

10. The method according to claim 9, wherein the yield of the diazoalkane is approximately 90%.

11. The method according to claim 1, wherein the diazoalkane is diazomethane.

12. The method according to claim 1, wherein the N-alkyl-N-nitroso compound is a N-methyl-N-nitroso compound.

13. The method according to claim 1, wherein the by-product does not require purification after it has been recovered from the reaction mixture.

14. The method according to claim 1, wherein the organic by-product is used to produce a further N-alkyl-N-nitroso compound.

15. The method according to claim 1, wherein the organic by-product has the general formula:

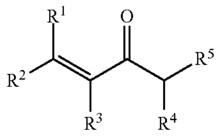

wherein RI, R2, R3 and R4 are hydrogen, alkyl, alkenyl, alkoxy, alkoxylate, alkyloxy, alkenyloxy or alkoxyalkyl groups and $R^5$ is hydrogen or an alkyl group.

16. The method according to claim 1, wherein the N-alkyl-N-nitroso compound is N-nitroso-β-methylaminoisobutyl methyl ketone (Liquizald) and wherein the organic by-product is mesityl oxide.

17. The method according to claim 1, wherein the reaction occurs in the presence of water.

* * * * *

UNITED STATES PATENT AND TRADEMARK OFFICE

CERTIFICATE OF CORRECTION

PATENT NO. : 9,593,073 B2
APPLICATION NO. : 14/373828
DATED : March 14, 2017
INVENTOR(S) : Lee Proctor It is certified that error appears in the above-identified patent and that said Letters Patent is hereby corrected as shown below:

In the Claims

In Column 16, Claim 1, Line 66, after “wherein” replace “RI,” with --R1,--.

In Column 18, Claim 15, Line 19, after “wherein” replace “RI,” with --R1,--.

Signed and Sealed this
Twenty-third Day of May, 2017

Michelle K. Lee
*Director of the United States Patent and Trademark Office*